United States Patent [19]
Tanaka et al.

[11] Patent Number: 6,160,185
[45] Date of Patent: Dec. 12, 2000

[54] PROCESS FOR PURIFICATION OF METHYLAL

[75] Inventors: Yoshio Tanaka; Shigeru Yamamoto, both of Kurashiki, Japan

[73] Assignee: Asahi Kasei Kogyo Kabushiki Kaisha, Osaka, Japan

[21] Appl. No.: 08/831,285

[22] PCT Filed: Sep. 28, 1995

[86] PCT No.: PCT/JP95/01974

§ 371 Date: Mar. 31, 1997

§ 102(e) Date: Mar. 31, 1997

[87] PCT Pub. No.: WO96/11178

PCT Pub. Date: Apr. 18, 1996

[51] Int. Cl.[7] .................................................. C07C 41/56
[52] U.S. Cl. ............................ 568/594; 568/591; 203/75
[58] Field of Search ..................................... 568/591, 594; 203/75

[56] References Cited

U.S. PATENT DOCUMENTS 4,421,535 12/1983 Mehra ......................................... 62/17

FOREIGN PATENT DOCUMENTS

| 1127339 | 4/1962 | Germany . |
|---|---|---|
| 36-14460 | 8/1961 | Japan . |
| 56-147739 | 11/1981 | Japan . |
| 58-103331 | 6/1983 | Japan . |
| 3-56134 | 3/1991 | Japan . |

OTHER PUBLICATIONS

European Search Report for European Application No. EP 95932927, Jul. 10, 1997.

*Primary Examiner*—Shailendra Kumar
*Assistant Examiner*—Sreeni Padmanabhan
*Attorney, Agent, or Firm*—Pennie & Edmonds LLP

[57] ABSTRACT

Provided is a process for high purification of methylal by removing water and methanol present as impurities from the methylal. The process for purification of methylal comprises subjecting a methylal gas containing water and methanol and a polyalkylene glycol or a derivative thereof to gas-liquid counter current contact to remove the water and methanol.

16 Claims, 1 Drawing Sheet

PROCESS FOR PURIFICATION OF METHYLAL

This is the U.S. National Stage Application of PCT/JP95/01974 filed Sep. 28, 1995 now WO96/11178 published Apr. 18, 1996.

TECHNICAL FIELD

Methylal is used as a molecular weight modifier for polyacetal resin. It is known that when methylal containing impurities such as water, methanol and the like is used in such an application, the resulting polyacetal resin gives rise to reduction in molecular weight and quality deterioration.

The present invention relates to a process for purification of methylal, which process comprises removing water and methanol as impurities present in methylal to obtain high-purity methylal.

BACKGROUND ART

For obtaining high-purity methylal, there is a process using a molecular sieve made of synthetic zeolite or the like. This process, however, needs a very large amount of synthetic zeolite when a large amount of methylal is purified on an industrial scale. Moreover, in the process, since the adsorptivity of synthetic zeolite is deteriorated with the proceeding of the adsorption, regeneration of synthetic zeolite is necessary at a certain timing. The regeneration is conducted by heating the used synthetic zeolite at 250–300° C. and passing nitrogen therethrough to remove the adsorbed water. Thus, much labor and energy are required and the process using synthetic zeolite is not convenient.

JP-A-56-147739 discloses a process for purification of methylal by adding water to crude methylal containing methanol and subjecting the mixture to distillation to separate and remove the methanol. According to the Example of the literature, however, it is prerequisite for the process that the content of methanol as impurity in crude methylal is high, and the methanol content is certainly reduced from 6.9% by weight to 1.1% by weight. Meanwhile, water also present in crude methylal forms an azeotropic mixture with methylal or methanol; therefore, it is impossible to obtain methylal containing water in an amount as small as 0.7% by weight or less.

It is well known that a polyacetal resin can be obtained by copolymerizing trioxane with ethylene oxide, dioxolan or butanediolformal. For example, in JP-B-36-14460 is disclosed copolymerization between trioxane and ethylene oxide or between trioxane and a cyclic formal (e.g. dioxolan, 1,4-butanediolformal). It is also well known that in this copolymerization, methylal is used as a molecular weight modifier. Since methylal contains impurities such as water, methanol and the like and these impurities invite molecular weight reduction and quality deterioration of produced polyacetal resin, it is desired to develop a process for purifying methylal to a higher purity. Since methylal forms an azeotropic mixture with water and methanol [the azeotropic point between methylal and water: 42.3° C. (water content: 1.4% by weight), the azeotropic point between methylal and methanol: 42.3° C. (methanol content: 7.8% by weight)], it is impossible to separate methylal from the mixture by simple distillation.

It has been a problem to be solved in the art to simply separate and remove water and methanol as impurities present in methylal on an industrial scale to obtain high-purity methylal.

DISCLOSURE OF THE INVENTION

The present inventors made an intensive study on an industrial process for purification of methylal. As a result, the present inventors found out a process for purification of methylal, which can yield high-purity methylal very simply by using, during methylal purification, a polyalkylene glycol or a derivative thereof both having a high boiling point and forming no azeotropic mixture with methylal.

The present invention relates to a process for purification of methylal, which comprises subjecting a methylal gas containing impurities such as water, methanol and the like, the gas being formed by heating or the like, and a polyalkylene glycol or a derivative thereof, to gas-liquid counter current contact to remove the water and methanol present.

BEST MODE FOR CARRYING OUT THE INVENTION

Figure 1:
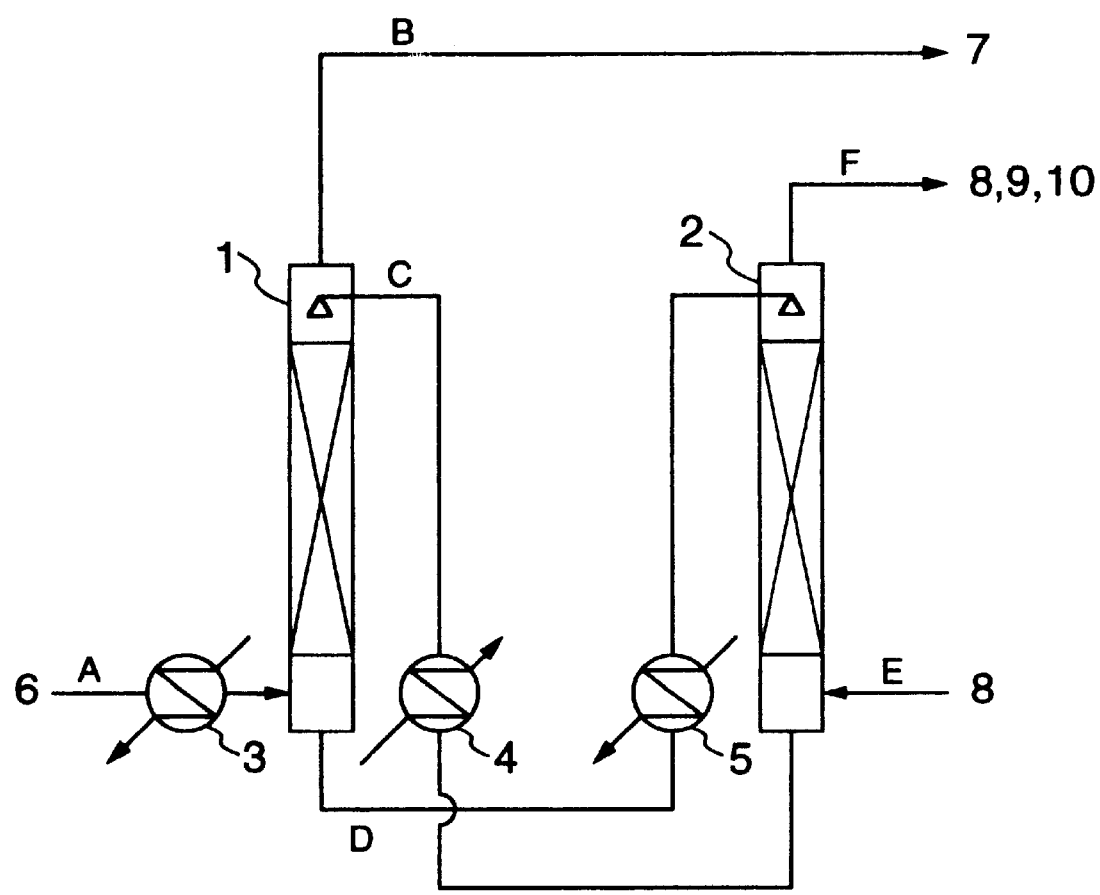
FIG. 1 is a flow diagram showing an example of the process for methylal purification, of the present invention.

The methylal treatable in the present process for methylal purification contains, as impurities, 0.1–5% by weight of water and 0.01–8% by weight of methanol and may further contain small amounts of other impurities such as methyl formate and the like. The present process is particularly effective for methylal containing 1.0–2.0% by weight, particularly 1.0–1.4% by weight of water and 0.1–7.8% by weight of methanol because such methylal forms an azeotropic mixture and the impurities contained therein cannot be separated by ordinary distillation.

The polyalkylene glycol used in the present invention includes polyethylene glycols such as diethylene glycol, triethylene glycol, tetraethylene glycol, etc.; polyethylene glycols containing 5 or more of oxyethylene units; polytetramethylene glycol and the like. The derivative of the polyalkylene glycol is a compound obtained by replacing a terminal hydroxyl group(s) of the above-mentioned polyalkylene glycol with an alkyl ester group, an aryl ester group, an alkyl ether group or an aryl ether group. A polyethylene glycol of high hydrophilicity or a diacetate or dimethyl ether thereof is preferred.

The polyalkylene glycol or a derivative thereof has a molecular weight of 200–800, preferably 300–500.

Methylal is fed at a temperature of 30–70° C., preferably 40–45° C.

The polyalkylene glycol or a derivative thereof is fed at a temperature of 40–100° C. When the temperature is too low, the yield of purified methylal is low; when the temperature is too high, the water content of purified methylal is high. Therefore, the temperature is preferably 70–90° C.

The gas-liquid counter current contact is conducted in an apparatus such as packed tower, plate tower, spray tower, wetted wall tower, bubble tower or the like. When a packed tower is used, the operation is conducted at atmospheric pressure to 5 kg/cm$^2$ G, and a polyalkylene glycol or a derivative thereof is fed in a 1- to 10-fold amount by weight relative to that of crude methylal, that is the total amount of methylal, water and methanol. Since about 8–12% by weight of the methylal fed is absorbed by the polyalkylene glycol or derivative thereof at 80° C., the amount of polyalkylene glycol or derivative thereof fed is preferably small, i.e. 2–4 times by weight the amount of crude methylal fed.

The gas-liquid contact is conducted, for example, by (i) a method of allowing a polyalkylene glycol or a derivative thereof to flow down in a liquid film state in a packed tower along the surfaces of the packings of the tower and allowing a methylal gas containing water and methanol, to rise in the tower through the gaps between the packings, to bring them in mutual contact;

(ii) a method of spraying a polyalkylene glycol or a derivative thereof into a methylal gas containing water and methanol;

(iii) a method of allowing a polyalkylene glycol or a derivative thereof to flow down in a liquid film state in a vertical round tube along the inner wall and allowing a methylal gas containing water and methanol, to rise in the central portion of the tube, to bring them in mutual contact; or the like. Preferably, method (i) using a packed tower is employed.

The polyalkylene glycol or derivative thereof containing water, methanol and methylal can be regenerated by subjecting said glycol or derivative to stripping using nitrogen. The polyalkylene glycol or derivative thereof after stripping contains water, methanol and methylal in a very small amount of about several ppm to about 100 ppm and can be fed again into the apparatus for methylal purification. The methanol and methylal separated by stripping can be recovered by condensation.

When a packed tower is used as the apparatus for gas-liquid counter current contact, the height of the tower can be experimentally determined depending upon the properties of packing, the ratio of polyalkylene glycol or derivative thereof fed to crude methylal fed, and the intended degree of methylal purification.

An example of the flow diagram of methylal purification according to the present process is shown in FIG. 1. In FIG. 1, crude methylal 6 containing water and methanol, flowing through a line A is vaporized by a heater 3 and then is fed into the bottom of a packed tower 1. A dehydrated polyalkylene glycol or derivative thereof flowing through a line C is fed into the top of the packed tower 1. Purified methylal 7 is obtained through a line B connected to the top of the packed tower 1. A polyalkylene glycol or derivative thereof containing water and methanol is drawn out through a line D connected to the bottom of the packed tower 1, is heated by a heater 5, and is fed into the top of a packed tower 2. Nitrogen 8 is fed into the packed tower 2 through a line E connected to the bottom of the packed tower 2, to remove water 9 and methanol 10 from the polyalkylene glycol or derivative thereof fed into the packed tower 2. A dehydrated and methanol-removed polyalkylene glycol or derivative thereof is drawn out from the bottom of the packed tower 2 and is fed again into the top of the packed tower 1 through a line C via a cooler 4.

The present invention is illustrated by means of Examples. The Examples, however, should not be construed as limiting the scope of the present invention.

EXAMPLE 1

A crude methylal solution containing 98.3% by weight of methylal, 1.14% by weight of water, 0.2% by weight of methanol and 0.36% by weight of methyl formate was vaporized by heating and fed, at a rate of 0.82 kg/hr, into the bottom of a packed tower of 50 mm (inside diameter) and 2.5 m (height) having a packing (structured packings, material: SUS316L, model: sheet 500S, trade name: MC Pack, manufacturer: Mitsubishi Kasei Engineering Company). Into the top of the tower was fed, at a rate of 4.68 kg/hr, polyethylene glycol dimethyl ether (number-average molecular weight: 300) containing 300 ppm of water, with the temperature being controlled at 80° C. The gas obtained from the tower top was purified methylal having a composition consisting of 99.4% by weight of methylal, 0.26% by weight of water, 0.01% by weight of methanol and 0.33% by weight of methyl formate. The liquid drawn out from the tower bottom had a composition consisting of 88.36% by weight of the polyethylene glycol dimethyl ether, 0.2% by weight of water, 0.04% by weight of methanol and 11.4% by weight of methylal. The gas chromatograph used for analysis was GC-8A and GC-14A both manufactured by Shimadzu Corporation.

EXAMPLE 2

A crude methylal solution containing 98.3% by weight of methylal, 1.14% by weight of water, 0.2% by weight of methanol and 0.36% by weight of methyl formate was vaporized by heating and fed, at a rate of 1.64 kg/hr, into the bottom of the same packed tower as used in Example 1. Into the top of the tower was fed, at a rate of 4.8 kg/hr, sufficiently dehydrated polyethylene glycol dimethyl ether containing 64 ppm of water, with the temperature being controlled at 80° C. The gas obtained from the tower top was purified methylal having a composition consisting of 99.5% by weight of methylal, 0.06% by weight of water, 0.07% by weight of methanol and 0.37% by weight of methyl formate. The liquid drawn out from the tower bottom had a composition consisting of 88.3% by weight of the polyethylene glycol dimethyl ether, 0.3% by weight of water, 0.04% by weight of methanol and 11.36% by weight of methylal.

EXAMPLE 3

A crude methylal solution containing 98.3% by weight of methylal, 1.11% by weight of water, 0.32% by weight of methanol and 0.27% by weight of methyl formate was vaporized by heating and fed, at a rate of 1.23 kg/hr, into the bottom of a packed tower of 50 mm (inside diameter) and 1.0 m (height) having a packing (structured packings, material: SUS316L, model: sheet 500S, trade name: MC Pack, manufacturer: Mitsubishi Kasei Engineering Company). Into the top of the tower was fed, at a rate of 11.0 kg/hr, polyethylene glycol monoacetate (number-average molecular weight: 300) containing 300 ppm of water, with the temperature being controlled at 80° C. The gas obtained from the tower top was purified methylal having a composition consisting of 99.5% by weight of methylal, 0.14% by weight of water, 0.09% by weight of methanol and 0.27% by weight of methyl formate. The liquid drawn out from the tower bottom had a composition consisting of 91.9% by weight of the polyethylene glycol monoacetate, 0.14% by weight of water, 0.03% by weight of methanol and 7.9% by weight of methylal. The gas chromatograph used for analysis was GC-8A and GC-14A both manufactured by Shimadzu Corporation.

Industrial Applicability

The high-purity methylal containing very small amounts of water and methanol as impurities obtained by the present process for methylal purification, can be used as a molecular weight modifier for polyacetal resin without inviting the molecular weight reduction and quality deterioration of the resin.

What is claimed is:

1. A process for purification of methylal, which process comprises subjecting a methylal gas containing water and methanol and a polyalkylene glycol or a derivative thereof having a molecular weight of 200–800 selected from the group consisting of polyalkylene glycol, mono- or di-alkyl ether of polyalkylene glycol, mono- or di-aryl ether of polyalkylene glycol, mono- or di-alkyl ester of polyalkylene glycol, and mono- or di-aryl ester of polyalkylene glycol, and mixtures thereof to gas-liquid counter current contact to remove the water and methanol.

2. A process according to claim 1, wherein the methylal to be purified contains 0.1–5% by weight of water.

3. A process according to claim 1, wherein the methylal to be purified contains 1.0–2.0% by weight of water.

4. A process according to claim 1, wherein the methylal to be purified contains 1.0–1.4% by weight of water.

5. A process according to claim 1, wherein the gas-liquid counter current contact is conducted in a packed tower at atmospheric pressure to 5 kg/cm² G.

6. A process according to claim 1, wherein the gas-liquid contact is conducted by a method of allowing a polyalkylene glycol or a derivative thereof to flow down in a liquid film state in a packed tower along the surfaces of the packings of the tower and allowing a methylal gas containing water and methanol, to rise in the tower through the gaps between the packings, to bring them in mutual contact.

7. A process according to claim 1, wherein the polyalkylene glycol or derivative thereof fed for the gas-liquid counter current contact has a temperature of 40–100° C. and is contacted with the methylal gas in an amount of 1–10 parts by weight per part by weight of the methylal gas.

8. A process according to claim 1, wherein the polyalkylene glycol or derivative thereof after the gas-liquid counter current contact is subjected to stripping using nitrogen, to separate and remove the water, methanol and methylal present therein, thereby regenerating said polyalkylene glycol or derivative thereof for reuse in methylal purification.

9. A process according to claim 1, wherein said polyalkylene glycol or a derivative thereof is flown down on a surface of packings in a tower and brought into contact with a methylal gas containing water and methanol, thereby causing said methylal to rise in the tower through gaps between the packings.

10. A method of purifying crude methylal comprising methylal, methanol and water, comprising:

heating the crude methylal to a temperature of about 30–70° C. to form a crude methylal gas;

introducing said crude methylal gas into a lower portion of a reaction tower such that said crude methylal gas rises within said tower;

introducing a solvent comprising polyalkylene glycol, or a derivative thereof, into an upper portion of said reaction tower at a temperature between 40–100° C., such that said solvent descends in the tower, thereby removing at least a portion of said methanol and water from the crude methylal gas during gas-liquid counter current contact, said solvent having a molecular weight between 200–800;

drawing off a purified methylal solution comprising at least 99% methylal from said tower.

11. The method according to claim 10, wherein the crude methylal is heated to between 40–45° C. and the solvent is heated to a temperature between 70–90° C.

12. The method according to claim 10, wherein the solvent is sprayed into the crude methylal gas.

13. The method according to claim 10, wherein the solvent is selected from the group consisting of polyalkylene glycol, mono- or di-alkyl ether of polyalkylene glycol, mono- or di-aryl ether of polyalkylene glycol, mono- or di-alkyl ester of polyalkylene glycol, and mono- or di-aryl ester-of polyalkylene glycol, and mixtures thereof.

14. The method according to claim 13, wherein the solvent has a molecular weight of 300–500.

15. The method according to claim 13, wherein the crude methylal is heated to between 40–45° C. and the solvent is heated to a temperature between 70–90° C.

16. A process according to claim 10, wherein the solvent is flown down on a surface of packings in a tower and brought into contact with said methylal gas, thereby causing said methylal to rise in the tower through gaps between the packings.

* * * * *

UNITED STATES PATENT AND TRADEMARK OFFICE
CERTIFICATE OF CORRECTION

PATENT NO. : 6,160,185
DATED : December 12, 2000
INVENTOR(S) : Yoshio Tanaka, Shigeru Yamamoto It is certified that error appears in the above-identified patent and that said Letters Patent is hereby corrected as shown below:

<u>Title page,</u>
Please insert the reference to the foreign application priority as follows:

-- [30]     Foreign Application Priority Data
October 7, 1994   [JP]   Japan ......................... 6-243662 --.

Signed and Sealed this

Twenty-third Day of October, 2001

*Attest:*

*Attesting Officer*

NICHOLAS P. GODICI
*Acting Director of the United States Patent and Trademark Office*